United States Patent
Ko et al.

(10) Patent No.: US 8,862,199 B2
(45) Date of Patent: Oct. 14, 2014

(54) ELECTRODE MEMBER AND APPARATUS FOR MEASURING BIOSIGNAL INCLUDING THE ELECTRODE MEMBER

(75) Inventors: Byung-hoon Ko, Hwaseong-si (KR); Hyung-sok Yeo, Hwaseong-si (KR); Jung-bae Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 150 days.

(21) Appl. No.: 13/213,569

(22) Filed: Aug. 19, 2011

(65) Prior Publication Data

US 2012/0172695 A1 Jul. 5, 2012

(30) Foreign Application Priority Data

Jan. 3, 2011 (KR) .................. 10-2011-0000118

(51) Int. Cl.
*A61B 5/04* (2006.01)
*A61B 1/00* (2006.01)

(52) U.S. Cl.
CPC ........... *A61B 5/04* (2013.01); *A61B 2562/0209* (2013.01); *A61B 2562/046* (2013.01)
USPC ............................ 600/372; 600/391; 607/152

(58) Field of Classification Search
CPC .... A61B 5/04087; A61B 5/6833; A61N 1/00; A61N 1/0404; A61N 1/0492; A61N 1/0496
USPC ................. 600/372, 382–384, 386, 391–396, 600/508–509; 607/149, 152
See application file for complete search history.

(56) References Cited

U.S. PATENT DOCUMENTS

| | | | | |
|---|---|---|---|---|
| 4,685,467 A * | 8/1987 | Cartmell et al. | ............... | 600/385 |
| 4,838,273 A | 6/1989 | Cartmell | | |
| 5,520,180 A | 5/1996 | Uy et al. | | |
| 6,341,504 B1 * | 1/2002 | Istook | .......... | 66/172 E |
| 6,701,172 B2 * | 3/2004 | Katzenmaier et al. | ........ | 600/391 |
| 7,206,630 B1 * | 4/2007 | Tarler | ............ | 600/509 |
| 8,457,709 B2 * | 6/2013 | Matthews et al. | ............. | 600/383 |
| 2002/0045836 A1 * | 4/2002 | Alkawwas | ..................... | 600/509 |
| 2007/0249946 A1 * | 10/2007 | Kumar et al. | .................. | 600/515 |
| 2009/0076363 A1 * | 3/2009 | Bly et al. | ........................ | 600/372 |
| 2009/0292193 A1 | 11/2009 | Wijesiriwardana | | |
| 2011/0279963 A1 * | 11/2011 | Kumar et al. | ............ | 361/679.31 |

FOREIGN PATENT DOCUMENTS

| | | |
|---|---|---|
| JP | 11-113864 | 4/1999 |
| KR | 10-2004-0095336 | 11/2004 |
| KR | 20-0428059 | 10/2006 |
| KR | 10-2007-0043124 A | 4/2007 |

\* cited by examiner

*Primary Examiner* — Linda Dvorak
*Assistant Examiner* — Brian M Antiskay
(74) *Attorney, Agent, or Firm* — NSIP Law

(57) ABSTRACT

An electrode member for a body is provided. The electrode member includes a first sheet member having at least one hole formed therein, at least one second sheet member respectively disposed in the at least one hole, at least one metal contact point disposed on the first sheet member, and at least one electrode respectively disposed on the at least one second sheet member.

29 Claims, 5 Drawing Sheets

ELECTRODE MEMBER AND APPARATUS FOR MEASURING BIOSIGNAL INCLUDING THE ELECTRODE MEMBER

CROSS-REFERENCE TO RELATED APPLICATIONS

This application claims the benefit of Korean Patent Application No. 10-2011-0000118, filed on Jan. 3, 2011, in the Korean Intellectual Property Office, the entire disclosure of which is incorporated herein by reference for all purposes.

BACKGROUND

1. Field

The following description relates to an electrode member and an apparatus for measuring a biosignal including the electrode member.

2. Description of the Related Art

A body is a type of conductor, and a number of minute electric currents may be generated in the body. Accordingly, an inner condition of the body may be measured by detecting the minute electric currents or sensing changes in the minute electric currents in response to external stimuli in the body. By using such a mechanism, biosignals such as electrocardiogram (ECG), electromyogram (EMG), electroencephalogram (EEG), galvanic skin resistance (GSR), electro-oculogram (EOG), body temperature, heartbeat pulse, blood pressure, and body movement may be measured, and an electrode for the body may be used to detect changes in such biosignals. For example, an electrode for a body may be directly attached to a user's skin, and also may be connected to a measurement system. Use and attempts to enhance user convenience and improve the quality of a biosignal measured by such an electrode are being actively conducted.

SUMMARY

In one general aspect, an electrode member for a body is provided. The electrode member includes a first sheet member having at least one hole formed therein, at least one second sheet member respectively disposed in the at least one hole, at least one metal contact point disposed on the first sheet member, and at least one electrode respectively disposed on the at least one second sheet member.

The at least one second sheet member may be spaced apart from the first sheet member.

The second sheet member may be connected to the first sheet member via at least one connection portion extending from one region of the first sheet member.

The first sheet member may be formed of a non-conductive material.

The second sheet member may be formed of a conductive material.

The electrode member may include first adhesive layers disposed on a top surface and a bottom surface of the first sheet member.

The first adhesive layers may be formed of a non-conductive adhesive material or a biomimetic adhesive.

The electrode member may include second adhesive layers disposed on a top surface and a bottom surface of the second sheet member.

The second adhesive layers may be formed of a conductive adhesive material.

The electrode member may include a connection line that connects the at least one metal contact point and the at least one electrode.

The connection line may have a square wave shape.

In cross-section view, the combined height of the at least one sheet member and the at least one second sheet member may be less than the height of the first sheet member.

In plan view, the first sheet member may have an L shape.

In another aspect, an apparatus for measuring a biosignal is provided. The apparatus includes an electrode member for a body, the electrode member comprising a first sheet member having at least one hole formed therein, at least one second sheet member respectively disposed in the at least one hole, at least one metal contact point disposed on the first sheet member, and at least one electrode respectively disposed on the at least one second sheet member, and a signal processing module comprising an analog signal processing unit that processes an analog signal transmitted from the electrode member, an analog-to-digital (A/D) signal converting unit that converts the analog signal into a digital signal, and a digital signal processing unit that processes the digital signal.

The signal processing module may further include a wired/wireless transmission unit that transmits the digital signal processed by the digital signal processing unit to an external device.

The signal processing module may further include at least one terminal electrically connected to the analog signal processing unit.

The at least one metal contact point may contact and may be electrically connected to the at least one terminal.

The at least one electrode may be spaced apart from the signal processing module.

The at least one second sheet member may be spaced apart from the first sheet member.

The second sheet member may be connected to the first sheet member via at least one connection portion extending from one region of the first sheet member.

The first sheet member may be formed of a non-conductive material, and the second sheet member may be formed of a conductive material.

The apparatus may include first adhesive layers that are disposed on a top surface and a bottom surface of the first sheet member and may be each formed of a non-conductive adhesive material.

The apparatus may include second adhesive layers that are disposed on a top surface and a bottom surface of the second sheet member and may be each formed of a conductive adhesive material.

The signal processing module may contact the first adhesive layer disposed on the top surface of the first sheet member and may be structurally connected to the electrode member.

The apparatus may include a connection line that connects the at least one metal contact point and the at least one electrode.

The connection line may have a square wave shape.

The signal processing module may be disposed on the electrode member.

In yet another aspect, an electronic device is provided. The electronic device includes an apparatus for measuring a biosignal. The apparatus includes an electrode member includes a first sheet member having at least one hole formed therein, at least one second sheet member respectively disposed in the at least one hole and has at least one electrode disposed thereon, and at least one metal contact point disposed on the first sheet member, and a signal processing module configured to measure the biosignal. The signal processing module includes at least one terminal configured to communicate with the electrode member via the metal contact point.

Figure 1A:
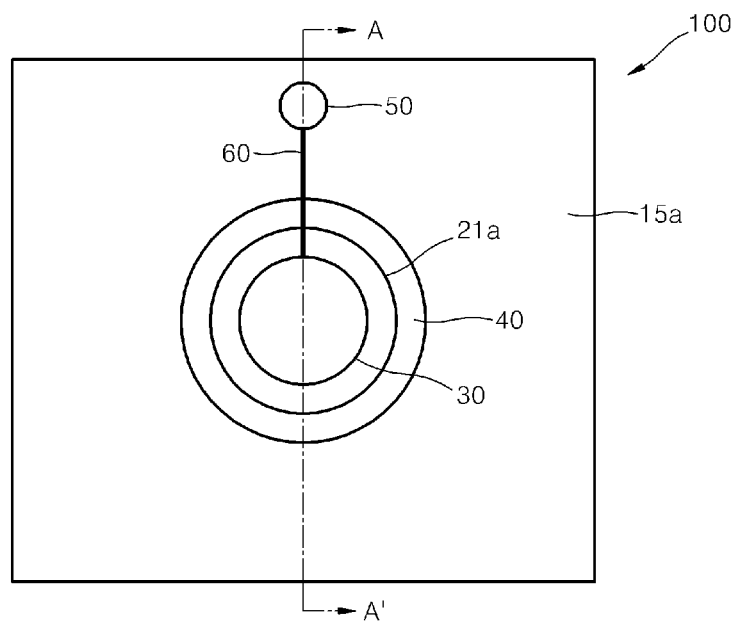
FIG. 1A illustrates a plan view of an example of an electrode member for a body.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

It is understood that, although the terms first, second, etc. may be used herein to describe various elements, these elements should not be limited by these terms. These terms are only used to distinguish one element from another. For example, a first element may be termed a second element, and, similarly, a second element may be termed a first element, without departing from the scope of the teachings herein. As used herein, the term "and/or," includes any and all combinations of one or more of the associated listed items.

It is also understood that when an element or layer is referred to as being "formed on," another element or layer, it may be directly or indirectly formed on the other element or layer. In other words, for example, intervening elements or layers may be present. In another example, in response to an element or layer being referred to as being "directly formed on," to another element, there are no intervening elements or layers present. Other words used to describe the relationship between elements or layers should be interpreted in a like fashion (for example, "between," versus "directly between," "adjacent," versus "directly adjacent," etc.).

It is further understood that the terminology used herein is not intended to be limiting of the examples. As used herein, the singular forms "a," "an," and "the," are intended to include the plural forms as well, unless the context clearly indicates otherwise. It is also understood that the terms "comprises," "comprising," "includes," and/or "including," when used herein, specify the presence of stated features, integers, steps, operations, elements, and/or components, but do not preclude the presence or addition of other features, integers, steps, operations, elements, and/or components.

Figure 1B:
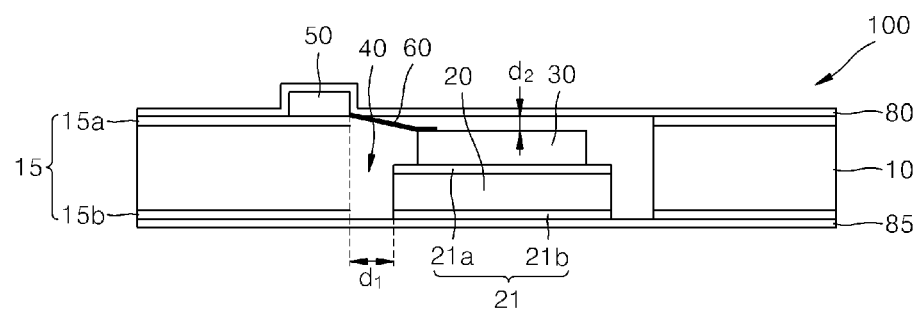
FIG. 1B illustrates a cross-sectional view of the example of the electrode member of FIG. 1A.

FIG. 1A illustrates a plan view of an example of an electrode member 100 for a body, for example, a living body. FIG. 1B illustrates a cross-sectional view of an example of the electrode member 100 taken along line AA' of FIG. 1A.

Referring to FIGS. 1A and 1B, the electrode member 100 may include a first sheet member 10 having at least one hole 40 formed therein, at least one second sheet member 20 respectively disposed in the at least one hole 40, at least one metal contact point 50 disposed on the first sheet member 10, and at least one electrode 30 respectively disposed on the at least one second sheet member 20.

The first sheet member 10 may be formed of a non-conductive material or an insulating material, for example, paper, fabric, polyethylene foam, or polyurethane foam. As a non-limiting example, the first sheet member 10 has a rectangular shape in FIG. 1A. As another example, the first sheet member 10 may have a circular shape or a polygonal shape. The at least one hole 40 may be formed in the first sheet member 10. The at least one hole 40 may be a through-hole passing through the first sheet member 10, and may have a circular or polygonal cross-section. Meanwhile, the second sheet member 20 may be disposed in the at least one hole 40.

First adhesive members 15a and 15b which are collectively referred to as a first adhesive member 15 may be respectively disposed on a top surface and a bottom surface of the first sheet member 10. The first adhesive member 15 may be formed of a non-conductive adhesive material or a non-conductive cohesionant, and may be formed by coating a non-conductive adhesive material on the top surface and the bottom surface of the first sheet member 10. Examples of the non-conductive adhesive material may include an acryl-based adhesive material and/or a silicon-based adhesive material. Meanwhile, the first adhesive layer 15 may be formed of a biomimetic adhesive or a biomimetic cohesionant. The biomimetic adhesive, which is included in a living organism or mimics a living organism-made adhesive, may be better in terms of biocompatibility as compared to other adhesives. Examples of the biomimetic adhesive may include gecko-feet based hairs, such as, microfibers, and mussel adhesive protein. Since a gecko has many microfiber-like hairs, an adhesive force may be generated by an attractive force (van der Waals' force) between the microfibers and an object (for example, a wall or skin). The mussel adhesive protein may exhibit an adhesive force high enough for a mussel to stick to a rock even in water, such as, in the sea. In this example, the biomimetic adhesive may be non-conductive. The first adhesive layer 15a disposed on the top surface of the first sheet member 10 may contact a signal processing module 350 (see FIG. 6), and the first adhesive layer 15b disposed on the bottom surface of the first sheet member 10 may contact a body. Also, the signal processing module 350 may be attachable and detachable to the first adhesive layer 15a, and the first adhesive layer 15b may be attachable and detachable to a skin of the body.

The second sheet member 20 may be disposed in the at least one hole 40 formed in the first sheet member 10. In other words, the second sheet member 20 may be disposed in the at least one hole 40 to be spaced apart from the first sheet member 10 by a predetermined interval $d_1$. Also, a thickness of the second sheet member 20 may be thinner than a thickness of the first sheet member 10. The second sheet member 20 may be formed of a conductive material or a conductive cohesionant. The second sheet member 20 may have a circular shape as shown in FIG. 1B, or may have a polygonal shape. Second adhesive layers 21a and 21b which are collectively referred to as a second adhesive layer 21 may be respectively disposed on a top surface and a bottom surface of the second sheet member 20. The second adhesive layer 21 may be formed of a conductive adhesive material, and may be formed by coating a conductive adhesive material on the top surface and the bottom surface of the second sheet member 20. The second adhesive layer 21a disposed on the top surface of the second sheet member 20 may contact the electrode 30, and the second adhesive layer 21b disposed on the bottom surface of the second sheet member 20 may contact the skin of the body. The second adhesive layer 21b may be attachable and detachable to the skin.

The metal contact point 50 may be disposed on the first sheet member 10, and may be disposed on the first adhesive layer 15a disposed on the top surface of the first sheet member 10. The metal contact point 50 may contact the first adhesive layer 15a and may be fixed to the first sheet member 10. As a non-limiting example, the metal contact point 50 has a contact point shape in FIGS. 1A and 1B. In another example, the metal contact point 50 may be an electrical connector having any of various other shapes.

The electrode 30 may be disposed on the second sheet member 20, and may be disposed on the second adhesive layer 21a disposed on the top surface of the second sheet member 20. The electrode 30 may be formed of a conductive material, for example, a metal such as silver (Ag), AgCl, gold (Au), or platinum (Pt). The electrode 30 may be electrically connected to the metal contact point 50 via a connection line 60 formed of a conductive material, for example, a metal. The electrode 30 may contact the second adhesive layer 21a, and may be structurally connected or fixed to the second sheet member 20. Since the second adhesive layer 21a is formed of a conductive material, the electrode 30 may be electrically connected to the second sheet member 20 via the second adhesive layer 21a. Accordingly, a biosignal may be transmitted to the electrode 30 via the second adhesive layer 21 and the second sheet member 20, and may be transmitted to the metal contact point 50 via the connection line 60.

The electrode 30 may be disposed on the second sheet member 20 that is spaced apart from the first sheet member 10 by the predetermined interval $d_1$. And a top surface of the electrode 30 may be spaced apart from a top surface of the first sheet member 10 or the first adhesive layer 15a by a predetermined interval $d_2$. In other words, the top surface of the electrode 30 may be lower than the top surface of the first sheet member 10 or the first adhesive layer 15a. Accordingly, the electrode member 100 may be less affected by a relative displacement due to expansion of the skin or movement of the body. In other words, even though a position the first sheet member 10, which contacts a large area of the skin, relative to a position of the second sheet member 20 is changed due to an external movement, the electrode 30 and the second sheet member 20 spaced apart from the first sheet member 10 may be less affected by the external movement. Also, the electrode member 100 may be electrically connected to the signal processing module 350 (see FIG. 6) via the metal contact point 50. Accordingly, since the electrode 30 having relatively large areas does not directly contact the signal processing module 350 (see FIG. 6), motion artifacts due to contact with a large area may be reduced.

A buffer structure including the first sheet member 10 and the second sheet member 20 which are spaced apart from each other separates an electrical connection and a mechanical connection between the electrode member 100 and the signal processing module 350 (see FIG. 6), thereby enabling the electrode member 100 to better withstand motion artifacts. The buffer structure may serve as a ventilation hole through which sweat is discharged from the skin to which the electrode member 100 is attached, and may reduce skin troubles by reducing an area contacting the skin.

Meanwhile, protective films 80 and 85 may be respectively disposed on a top surface and a bottom surface of the electrode member 100. The protective films 80 and 85 may prevent an adhesive force of the first adhesive layer 15 and the second adhesive layer 21 from being reduced, and a plurality of the electrodes 30 from contacting one another during storage. Also, the protective films 80 and 85 may support the second sheet member 20 that is spaced apart from the first sheet member 10 during manufacture or storage of the electrode member 100.

Figure 2A:
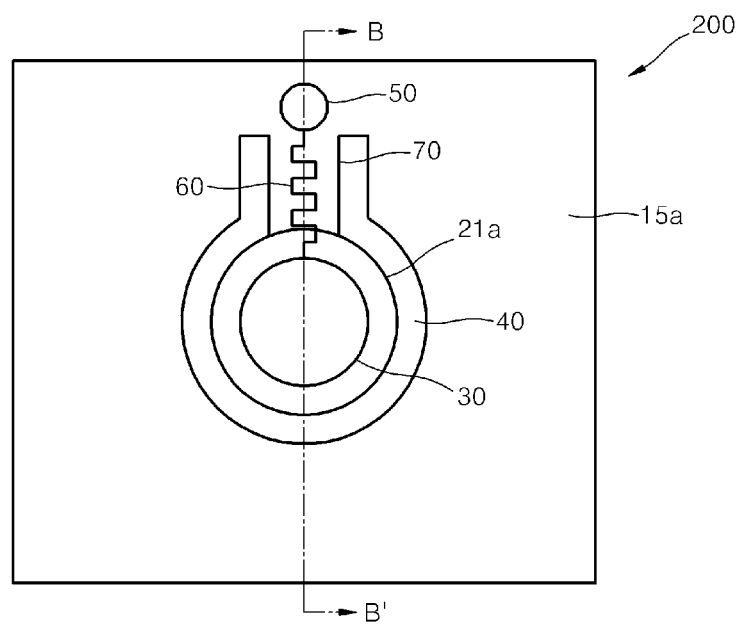
FIG. 2A illustrates a plan view of another example of an electrode member for a body.
Figure 2B:
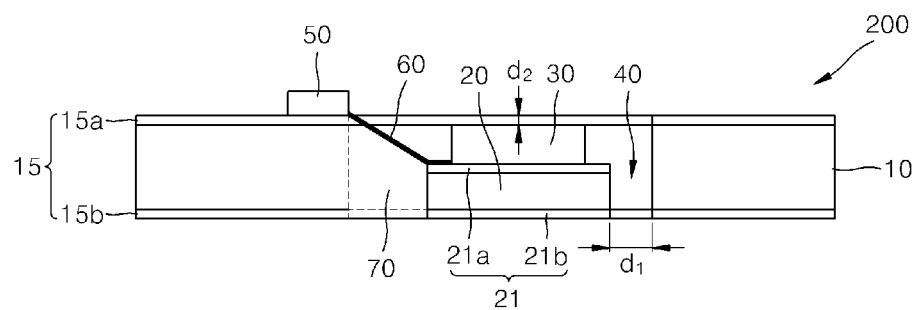
FIG. 2B illustrates a cross-sectional view of the example of the electrode member of FIG. 2A.

FIG. 2A illustrates a plan view of another example of an electrode member 200 for a body. FIG. 2B illustrates a cross-sectional view of the example of the electrode member 200 taken along line BB' of FIG. 2A. The following description will explain differences between the electrode member 100 and the second electrode member 200.

Referring to FIGS. 2A and 2B, the electrode member 200 may include the first sheet member 10 having at least one hole 40 formed therein, at least one second sheet member 20 respectively disposed in the at least one hole 40, at least one metal contact point 50 disposed on the first sheet member 10, and at least one electrode 30 respectively disposed on the at least one second sheet member 20.

The first sheet member 10 may be formed of a non-conductive material or an insulating material, such as, for example, paper, fabric, polyethylene foam, or polyurethane foam. The at least one hole 40 may be formed in the first sheet member 10, and the second sheet member 20 may be disposed in the at least one hole 40. The second sheet member 20 may be formed of a conductive material. In addition, the first adhesive layers 15a and 15b may be respectively disposed on a top surface and a bottom surface of the first sheet member 10, and the second adhesive layers 21a and 21b may be respectively disposed on a top surface and a bottom surface of the second sheet member 20.

The second sheet member 20 may be connected to the first sheet member 10 via at least one connection portion 70 extending from one region of the first sheet member 10. The connection portion 70 may help to attach the second sheet member 20 to the first sheet member 10 so that a movement of the first sheet member 10 has almost no effect on the second sheet member 20. In other words, the connection portion 70 may be formed to connect the first sheet member 10 and the second sheet member 20 such that each of the first and second sheet members 10 and 20 is not affected by the movement of the other sheet member. The connection portion 70 may be formed of a non-conductive material or an insulating material, similar to the first sheet member 10. A thickness of the connection portion 70 may be thinner than that of the first sheet member 10. Also, the connection portion 70 may be formed at a slant from the first sheet member 10 to the second sheet member 20. As another example, the connection portion 70 may be formed of a non-conductive elastic material.

The connection portion 70 may be formed by forming a trench in the first sheet member 10, or may be formed by extending from an inner surface of the at least one hole 40 formed in the first sheet member 10. A buffer structure including the first sheet member 10 and the second sheet member 20 which are connected to each other with a minimum contact may reduce motion artifacts that may be generated due to relative movements of the electrode member 200 and the signal processing module 350 (see FIG. 6).

The connection line 60 for connecting the metal contact point 50 and the electrode 30 may be disposed on the connection portion 70. The connection line 60 may have a square wave shape as shown in FIG. 2A, and may prevent relative movements of the second sheet member 20 and the electrode 30 from being transmitted to the metal contact point 50. In other words, movements of the second sheet member 20 and the electrode 30 may be offset by the connection line 60 having a square wave shape.

Figure 3:
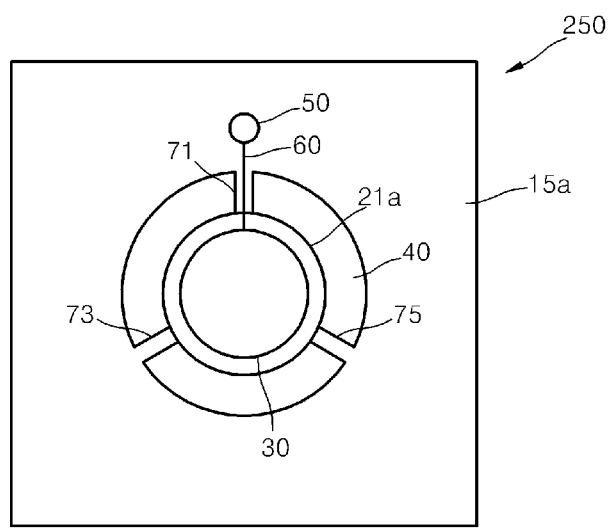
FIG. 3 illustrates a plan view of another example of an electrode member for a body.

FIG. 3 illustrates a plan view of another example of an electrode member 250 for a body. The following description will explain differences from the electrode members 100 and 200 of FIGS. 1 and 2.

Referring to FIG. 3, the electrode member 250 may include the first sheet member 10 (see FIG. 2B) having at least one hole 40 formed therein, at least one second sheet member 20 (see FIG. 2B) respectively disposed in the at least one hole 40, at least one metal contact point 50 disposed on the first sheet member 10, and at least one electrode 30 respectively disposed on the at least one second sheet member 20.

The first sheet member 10 may be formed of a non-conductive material or an insulating material, for example, paper, fabric, polyethylene foam, or polyurethane foam. The at least one hole 40 may be formed in the first sheet member 10, and the second sheet member 20 may be disposed in the at least one hole 40. The second sheet member 20 may be formed of a conductive material. In addition, the first adhesive layers 15a and 15b may be respectively disposed on a top surface and a bottom surface of the first sheet member 10, and the second adhesive layers 21a and 21b may be respectively disposed on a top surface and a bottom surface of the second sheet member 20.

The second sheet member 20 may be connected to the first sheet member 10 via three connection portions 71, 73, and 75 extending respectively from one region of the first sheet member 10. The connection portions 71, 73, and 75 may be formed to connect the first sheet member 10 and the second sheet member 20, such that each of the first sheet member 10 and the second sheet member 20 is not affected or minimally affected by the relative movement of the other sheet member. The connection portions 71, 73, and 75 may be formed of a non-conductive material or an insulating material, like the first sheet member 20, and may have a smaller thickness so as to be elastically deformed. As another example, the connection portions 71, 73, and 75 may be formed of an elastic material. Meanwhile, the connection portions 71, 73, and 75 may be formed by extending from an inner surface of the at least one hole 40.

Figure 6:
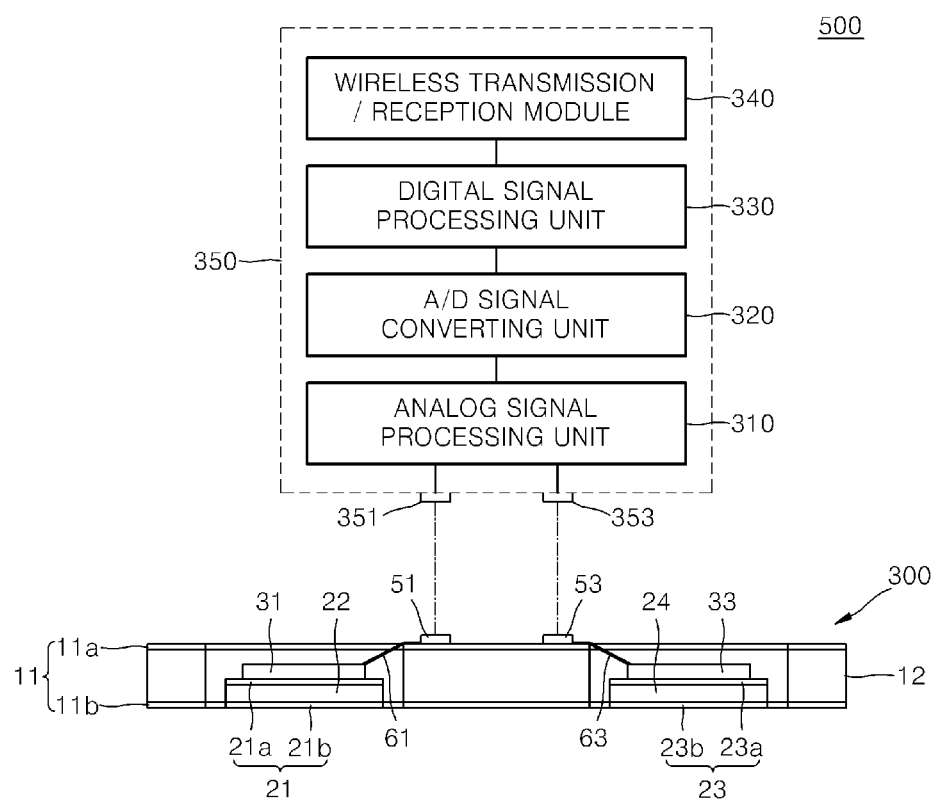
FIG. 6 illustrates a plan view of an example of an apparatus for measuring a biosignal.

A buffer structure including the first sheet member 10 and the second sheet member 20 which are connected to each other with a minimum contact may reduce motion artifacts that may be generated due to relative movements of the electrode member 250 and the signal processing module 350 (see FIG. 6).

Figure 4:
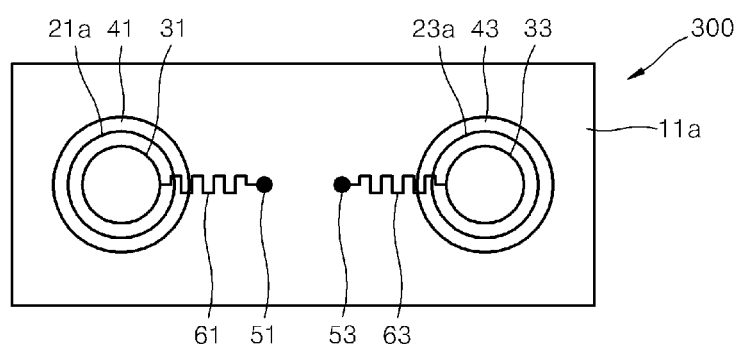
FIG. 4 illustrates a plan view of another example of an electrode member for a body.

FIG. 4 illustrates a plan view of another example of an electrode member 300 for a body. The following description will explain differences from the electrode members 100, 200, and 250 of FIGS. 1 through 3.

Referring to FIG. 4, the electrode member 300 may include the first sheet member 10 (see FIG. 2B) having first and second holes 41 and 43 formed therein, two second sheet members 20 (see FIG. 2B) respectively disposed in the first and second holes 41, and 43, first and second metal contact points 51 and 53 disposed on the first sheet member 10, and the first and second electrodes 31 and 33 respectively disposed on the two second sheet members 20. The first and second holes 41 and 43 may be formed in the first sheet member 10 to be spaced apart from each other. A first adhesive layer 11a may be disposed on the first sheet member 10, and second adhesive layers 21a and 23a may be respectively disposed on top surfaces of the two second sheet members 20. The first sheet member 10 may have a rectangular shape, and the second sheet members 20 may have circular shapes to be disposed in the first and second holes 41 and 43 to be spaced apart from each other. As another aspect, the first sheet member 10 is not limited to a rectangular shape, and the second sheet member 20 is not limited to a circular shape. The first and second sheet members 10 and 20 may be formed to have various other shapes.

The electrode member 300 may include the first and second electrodes 31 and 33. The first electrode 31 may be, for example, a ground electrode. In other words, the electrode member 300 may be used to measure an electrical signal, such as, a biosignal, between the second electrode 33 and the first electrode 31, the first electrode 31 being a ground electrode. For example, the electrode member 300 may be used to measure biosignals such as electrocardiogram (ECG), electromyogram (EMG), electroencephalogram (EEG), galvanic skin resistance (GSR), electrooculogram (EOG), body temperature, heartbeat pulse, blood pressure, and body movement.

The first and second electrodes 31 and 33 may be connected to the first and second metal contact points 51 and 53 via connection lines 61 and 63, respectively. The first and second metal contact points 51 and 53 may be electrically connected to the signal processing module 350 (see FIG. 6). The first adhesive layer 11a may be mechanically connected to the signal processing module 350 (see FIG. 6). Accordingly, an electrical connection and a mechanical connection between the electrode member 300 and the signal processing module 350 (see FIG. 6) are separated from each other, thereby reducing motion artifacts that may be generated due to relative movements of the electrode member 300 and the signal processing module 350.

Figure 5:
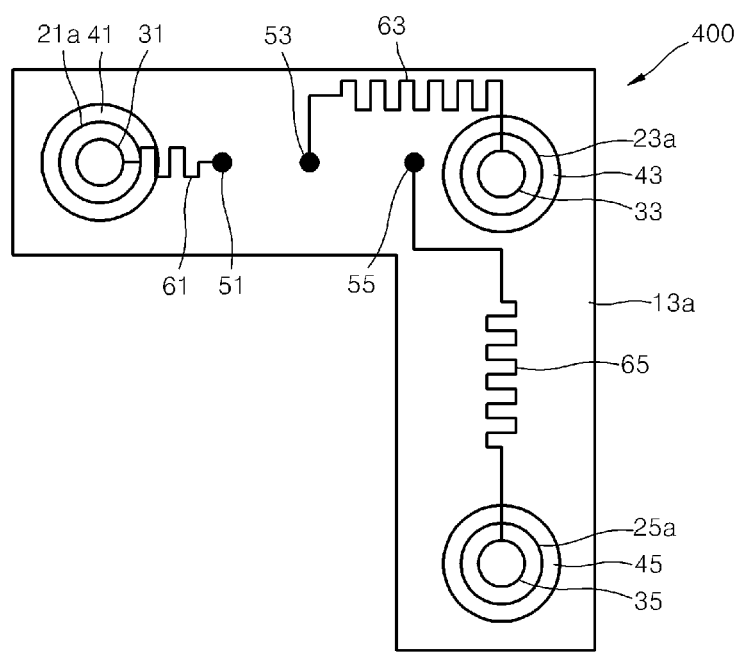
FIG. 5 illustrates a plan view of another example of an electrode member for a body.

FIG. 5 illustrates a plan view of another example of an electrode member 400 for a body. The following description will explain differences from the electrode members 100, 200, 250, and 300 of FIGS. 1 through 4.

Referring to FIG. 5, the electrode member 400 may include the first sheet member 10 (see FIG. 2B) having first through third holes 41, 43, and 45 formed therein, three second sheet members 20 (see FIG. 2B) respectively disposed in the first through third holes 41, 43, and 45, first through third metal contact points 51, 53, and 55 disposed on the first sheet member 10, and first through third electrodes 31, 33, and 35 respectively disposed on the three second sheet members 20. A first adhesive layer 13a may be disposed on the first sheet member 10, and second adhesive layers 21a, 23a, and 25a may be respectively disposed on top surfaces of the three second sheet members 20.

Although the first sheet member 10 disposed on a bottom surface of the first adhesive layer 13a has a "⌐" shape, the example is not limited thereto. In other words, the first sheet member 10 may have various other shapes based on the number of biosignals to be measured or the number of body parts to which the first sheet member 10 is to be attached. Accordingly, positions of the first through third holes 41, 43, and 45 formed in the first sheet member 10 may be determined in various ways, and positions of the second sheet members 20 disposed in the first through third holes 41, 43, and 45 may be determined in various ways.

The electrode member 400 may include the first through third electrodes 31, 33, and 35, and the first electrode 31 may be, for example, a ground electrode. That is, the electrode member 400 may be used to measure an electrical signal, such as, a biosignal between the first electrode 31 and the second electrode 33 and between the first electrode 31 and the third electrode 35. Accordingly, the electrode member 400 may be used to measure at least one biosignal of at least one body part. Meanwhile, the first through third electrodes 31, 33, and 35 may be connected to the first through third metal contact points 51, 53, and 55 via connection lines 61, 63, and 65, respectively, and the first through third metal contact points 51, 53, and 55 may be electrically connected to the signal processing module 350 (see FIG. 6). Accordingly, the electrode member 400 may measure at least one biosignal with reduced motion artifacts at at least one body part.

FIG. 6 illustrates a cross-sectional view of an example of an apparatus 500 for measuring a biosignal.

Referring to FIG. 6, the apparatus 500 may include the electrode member 300 and the signal processing module 350. The apparatus 500 may include any of the electrode members 100, 200, 250, and 400 instead of the electrode member 300 of FIG. 4. The apparatus 500 may measure various bio-electrical signals, such as, for example, ECG, EMG, EEG, GSR, EOG, body temperature, heartbeat pulse, blood pressure, and body movement.

The electrode member 300 may include a first sheet member 12 having the first and second holes 41 and 43 formed therein, two second sheet members 22 and 24 respectively disposed in the first and second holes 41 and 43, the first and second metal contact points 51 and 53 disposed on the first sheet member 12, and the first and second electrodes 31 and 33 respectively disposed on the two second sheet members 22 and 24. First adhesive layers 11a and 11b may be respectively disposed on a top surface and a bottom surface of the first sheet member 12, and second adhesive layers 21a and 21b which are collectively referred to as a second adhesive layer 21 and second adhesive layers 23a, and 23b which are collectively referred to as a second adhesive layer 23 may be respectively disposed on top surfaces and bottom surfaces of the two second sheet members 22 and 24.

The first sheet member 12 may be formed of a non-conductive material or an insulating material, such as, for example, paper, fabric, polyethylene foam, or polyurethane foam. The first and second holes 41 and 43 may be formed in the first sheet member 12, and may be through-holes passing through the first sheet member 12. In addition, the second sheet members 22 and 24 may be respectively disposed in the first and second holes 41 and 43. The first adhesive layers 11a and 11b, which are collectively referred to as a first adhesive layer 11, may be respectively disposed on the top surface and the bottom surface of the first sheet member 12. The first adhesive layer 11 may be formed of a non-conductive adhesive material or a non-conductive cohesionant and may be formed by coating a non-conductive adhesive material on the top surface and the bottom surface of the first sheet member 12. Meanwhile, the first adhesive layer 11a disposed on the top surface of the first sheet member 12 may contact the signal processing module 350, and the first adhesive layer 11b disposed on the bottom surface of the first sheet member 12 may contact the skin of the body.

The second sheet members 22 and 24 may be respectively disposed in the first and second holes 41 and 43 formed in the first sheet member 12. In other words, the second sheet members 22 and 24 may be disposed in the first and second holes 41 and 43 to be spaced part from the first sheet member 12 by a predetermined interval $d_1$. The second sheet members 22 and 24 may be formed of a conductive material, and may have circular or polygonal shapes. The second adhesive layers 21 and 23 may be disposed on the top surfaces and the bottom surfaces of the second sheet members 22 and 24. Meanwhile, the second adhesive layers 21a and 23a disposed on the top surfaces of the second sheet members 22 and 24 may contact the electrodes 31 and 33, and the second adhesive layers 21b and 23b disposed on the bottom surfaces of the second sheet members 22 and 24 may contact the skin of the body.

The first and second metal contact points 51 and 53 may be disposed on the first sheet member 12, and may be disposed on the first adhesive layer 11a disposed on the top surface of the first sheet member 12. The first and second metal contact points 51 and 53 may contact the first adhesive layer 11a and may be fixed to the first sheet member 12. Meanwhile, although the first and second metal contact points 51 and 53 have contact point shapes in FIG. 5, the example is not limited thereto. In another example, the first and second metal contact points 51 and 53 may be electrical connectors having various other shapes.

The first and second electrodes 31 and 33 may be respectively disposed on the second sheet members 22 and 24, and may be disposed on the second adhesive layers 21a and 23a disposed on the top surfaces of the second sheet members 22 and 24. The first and second electrodes 31 and 33 may contact the second adhesive layers 21a and 23a, and may be structurally connected or fixed to the second sheet members 22 and 24. The first and second electrodes 31 and 33 may be electrically connected to the first and second metal contact points 51 and 53 via the connection lines 61 and 63 each formed of a conductive material, such as, for example, a metal. Since the first and second electrodes 31 and 33 are disposed to be spaced apart from the first sheet member 12 and the signal processing module 350, the first and second electrodes 31 and 33 may be less affected by a relative displacement due to expansion or contraction of the skin or movement of the body.

Meanwhile, protective films (not shown) may be disposed on a top surface and a bottom surface of the electrode member 300. The protective films may prevent an adhesive force between the first adhesive layer 11 and the second adhesive layers 21 and 23 from being reduced, and may prevent the first and second electrodes 31 and 33 from contacting each other during storage. Also, the protective films may support the second sheet members 22 and 24 that are spaced apart from the first sheet member 12 during manufacture of the electrode member 300. The electrode member 300 may contact the signal processing module 350 and the skin after the protective films are removed.

The signal processing module 350 may be disposed on the electrode member 300, and may include an analog signal processing unit 310, an analog-to-digital (A/D) signal converting unit 320, and a digital signal processing unit 330. The signal processing module 350 may also include a wireless transmission/reception module 340, and one or more terminals 351 and 353 for electrically connecting the signal processing module 350 and the electrode member 300.

The analog signal processing unit 310 amplifies or filters an electrical signal of a body, such as, an analog signal, transmitted from the terminals 351 and 353, and transmits the amplified or filtered analog signal to the A/D signal converting unit 320. The A/D signal converting unit 320 converts the analog signal into a digital signal, and transmits the digital signal to the digital signal processing unit 330. The digital signal processing unit 330 processes the digital signal according to a predefined algorithm. The wireless transmitting unit module 340 may transmit the processed digital signal in a wireless manner to an external device. The signal processing module 350 may include a wired transmission/reception module (not shown) to transmit the processed digital signal in a wired manner to an external device. Meanwhile, the signal processing module 350 may store the processed digital signal in a memory (not shown).

The terminals 351 and 353 of the signal processing module 350 may be formed of a conductive material, for example, a metal such as silver (Ag), AgCl, gold (Au), or platinum (Pt). The terminals 351 and 353 may be disposed on a surface of the signal processing module 350, and may be connected to the first and second metal contact points 51 and 53 of the electrode member 300. In response to the signal processing module 350 moving in a state where the first and second electrodes 31 and 33 which have relatively large areas and the terminals 351 and 353 directly contact each other, a contact between the first and second electrodes 31 and 33 and the terminals 351 and 353 may be changed, thereby distorting a biosignal and reducing a signal-to-noise ratio (SNR) of the biosignal. Accordingly, since in the apparatus 500, the first and second electrodes 31 and 33 and the terminals 351 and 353 are not directly connected to each other, motion artifacts due to contact between the first and second electrodes 31 and 33 and the terminals 351 and 353 may be reduced.

The electrode member 300 and the signal processing module 350 may be electrically connected via the first and second metal contact points 51 and 53 and the terminals 351 and 353, and may be physically, mechanically or structurally connected by the first adhesive layer 11a. In other words, an electrical connection and a mechanical connection between the electrode member 300 and the signal processing module 350 are separated from each other. The electrode member 300 and the signal processing module 350 may be structurally connected to each other by various fastening means such as protrusions and grooves, Velcro, and magnets, instead of by or in addition to an adhesive layer. The second sheet members 22 and 24 and the first and second electrodes 31 and 33 may be disposed to be spaced apart from the first sheet member 12 and to be spaced apart from the signal processing module 350.

Such a buffer structure where the second sheet members 22 and 24 and the first and second electrodes 31 and 33 are spaced apart from the first sheet member 12 and the signal processing module 350 and an electrical connection and a mechanical connection between the electrode member 300 and the signal processing module 350 are separated from each other may make the apparatus 500 resistant to motion artifacts. In other words, even in response to the first sheet member 12 contacting a relatively large area of the skin moving due to movement of the body or expansion of the skin, affecting of the second sheet members 22 and 24 and the first and second electrodes 31 and 33 due to the movement may be prevented. Also, even in response to the signal processing module 350 moving due to an external impact, affecting of the second sheet members 22 and 24 and the first and second electrodes 31 and 33 due to the movement may be prevented. Accordingly, the apparatus 500 may increase an SNR.

In addition, the buffer structure may serve as a ventilation hole through which sweat is discharged from the skin to which the apparatus 500 is attached, and may reduce skin troubles by reducing a contact area with the skin. Meanwhile, in the apparatus 500, the electrode member 300 may be disposable, and the signal processing module 350 may be re-usable.

The apparatus 500 may be part of an electronic device for measuring the biosignal.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An electrode member for a body, the electrode member comprising:
    a first sheet member having at least one hole formed therein;
    at least one second sheet member disposed in the at least one hole of the first sheet member;
    at least one metal contact point disposed on the first sheet member; and
    at least one electrode disposed on the at least one second sheet member, the at least one metal contact point is spaced apart from the at least one electrode, and the at least one second sheet member is spaced apart from the first sheet member by an interval in the at least one hole of the first sheet member.

2. The electrode member of claim 1, wherein the second sheet member is connected to the first sheet member via at least one connection portion extending from one region of the first sheet member.

3. The electrode member of claim 1, wherein the first sheet member is formed of a non-conductive material.

4. The electrode member of claim 1, wherein the second sheet member is formed of a conductive material.

5. The electrode member of claim 1, further comprising first adhesive layers disposed on a top surface and a bottom surface of the first sheet member.

6. The electrode member of claim 5, wherein the first adhesive layers are formed of a non-conductive adhesive material or a biomimetic adhesive.

7. The electrode member of claim 1, further comprising second adhesive layers disposed on a top surface and a bottom surface of the second sheet member.

8. The electrode member of claim 7, wherein the second adhesive layers are formed of a conductive adhesive material.

9. The electrode member of claim 1, further comprising a connection line that connects the at least one metal contact point and the at least one electrode.

10. The electrode member of claim 9, wherein the connection line has a square wave shape.

11. An apparatus configured to measure a biosignal, the apparatus comprising:
    an electrode member, the electrode member comprising a first sheet member having at least one hole formed therein, at least one second sheet member disposed in the at least one hole of the first sheet member, at least one metal contact point disposed on the first sheet member, and at least one electrode disposed on the at least one second sheet member and the at least one second sheet member is spaced apart from the first sheet member by an interval in the at least one hole of the first sheet member, and the at least one metal contact point is spaced apart from the at least one electrode; and
    a signal processing module comprising an analog signal processing unit configured to process an analog signal transmitted from the electrode member, an analog-to-digital (A/D) signal converting unit configured to convert the analog signal into a digital signal, and a digital signal processing unit configured to process the digital signal.

12. The apparatus of claim 11, wherein the signal processing module further comprises a wired or wireless transmission unit that transmits the digital signal processed by the digital signal processing unit to an external device.

13. The apparatus of claim 11, wherein the signal processing module further comprises at least one terminal electrically connected to the analog signal processing unit.

14. The apparatus of claim 13, wherein the at least one metal contact point contacts and is electrically connected to the at least one terminal.

15. The apparatus of claim 11, wherein the at least one electrode is spaced apart from the signal processing module.

16. The apparatus of claim 11, wherein the second sheet member is connected to the first sheet member via at least one connection portion extending from one region of the first sheet member.

17. The apparatus of claim 11, wherein the first sheet member is formed of a non-conductive material, and the second sheet member is formed of a conductive material.

18. The apparatus of claim 11, further comprising first adhesive layers disposed on a top surface and a bottom surface of the first sheet member and are each formed of a non-conductive adhesive material.

19. The apparatus of claim 11, further comprising second adhesive layers disposed on a top surface and a bottom surface of the second sheet member and are each formed of a conductive adhesive material.

20. The apparatus of claim 18, wherein the signal processing module contacts the first adhesive layer disposed on the top surface of the first sheet member and is structurally connected to the electrode member.

21. The apparatus of claim 11, further comprising a connection line that connects the at least one metal contact point and the at least one electrode.

22. The apparatus of claim 21, wherein the connection line has a square wave shape.

23. The electrode member of claim 1, wherein in cross-section view, the combined height of the at least one electrode and the at least one second sheet member is less than the height of the first sheet member.

24. The electrode member of claim 1, wherein in plan view, the first sheet member has an L shape.

25. The apparatus of claim 11, wherein the signal processing module is disposed on the electrode member.

26. An electronic device, the electronic device comprising an apparatus configured to measure a biosignal, the apparatus comprising:
   an electrode member comprising
      a first sheet member having at least one hole formed therein;
      at least one second sheet member disposed in the at least one hole of the first sheet member and has at least one electrode thereon, and the at least one second sheet member is spaced apart from the first sheet member by an interval in the at least one hole of the first sheet member; and
      at least one metal contact point disposed on the first sheet member, and the at least one metal contact point is spaced apart from the at least one electrode; and
   a signal processing module configured to measure the biosignal, the signal processing module comprising at least one terminal configured to communicate with the electrode member via the metal contact point.

27. The electrode member of claim 1, wherein the top surface of the electrode is lower than the top surface of the first sheet member or lower than the surface of an adhesive layer.

28. The electrode member of claim 1, wherein the electrode is formed of one of silver (Ag), AgCl, gold (Au), or platinum (Pt).

29. The apparatus of claim 11, further comprising a buffer structure where the at least one second sheet member and at least one electrode are spaced apart from the first sheet member and the signal processing module.

* * * * *